United States Patent [19]

Pick

[11] 4,392,492

[45] Jul. 12, 1983

[54] APPARATUS FOR STORING AND DISPENSING LIQUID DOUCHE

[75] Inventor: Ernest Pick, Cos Cob, Conn.

[73] Assignee: The Purdue Frederick Company, Norwalk, Conn.

[21] Appl. No.: 282,254

[22] Filed: Jul. 10, 1981

[51] Int. Cl.³ .............................................. A61M 7/02
[52] U.S. Cl. ........................ 604/82; 206/219, 604/212
[58] Field of Search ............... 128/251, 248, 232, 272, 128/272.1, 272.3; 141/2, 5, 18, 311 R, 329; 206/219; 222/541

[56] References Cited

U.S. PATENT DOCUMENTS

| | | | |
|---|---|---|---|
| 1,641,328 | 9/1927 | Ferdinand | 141/18 |
| 2,798,488 | 7/1957 | Hall | 128/272 X |
| 3,064,802 | 11/1962 | Jess et al. | 206/219 |
| 3,184,121 | 5/1965 | Volckening | 222/541 X |
| 3,190,619 | 6/1965 | Penny et al. | 128/272.1 X |
| 3,802,434 | 4/1974 | Brooks | 128/251 |
| 3,857,423 | 12/1974 | Ronca, Jr. | 206/219 X |
| 3,917,120 | 11/1975 | Larenz et al. | 222/541 X |

Primary Examiner—John D. Yasko
Attorney, Agent, or Firm—Steinberg & Raskin

[57] ABSTRACT

Apparatus for storing and dispensing a medicated douche solution includes a sealed unitary packette as one of its components and which has a predetermined volume of liquid douche concentrate stored within a sealed interior volume defined thereby. The packette is formed of thin flexible plastic material and includes a container portion in which the douche concentrate is stored and a dispenser portion integral with the container portion and which is constituted by an elongated, small diameter tubular stem which has a constant transverse cross-section throughout its length and a separable terminal tip portion. The packette is openable through separation of the terminal tip portion from the dispenser portion whereupon the dispenser portion is inserted through an opening of a bottle containing a diluent so as to extend to a significant extent into the interior thereof. The concentrate is dispensed into the diluent by squeezing the container portion of the packette. An elongate nozzle is then connected to the bottle for subsequent administration of the douche solution.

12 Claims, 5 Drawing Figures

APPARATUS FOR STORING AND DISPENSING LIQUID DOUCHE

BACKGROUND OF THE INVENTION

This invention relates generally to apparatus for administering douche solutions and, more particularly, to apparatus for storing and dispensing douche components for administration of a medicated douche solution.

Apparatus are known for administering medicated douche solution for the temporary relief of minor vaginal irritation or itching. In particular, one type of such apparatus includes a sealed bottle containing a diluent such as sanitized water, a nozzle adapted to be connected to the bottle and which is slanted for facilitating use, and a small funnel-shaped vial containing a douche concentrate. In order to form the medicated douche solution, an opening is formed in the diluent bottle whereupon the concentrate containing vial is opened by breaking the top off at its neck. The vial is then inverted and the opened tip quickly associated with the bottle opening whereupon the vial is squeezed and the concentrated liquid dispensed into the diluent in the bottle. The nozzle is then connected to the top of the bottle and the douche solution administered.

The above-described apparatus as well as other types of similar apparatus are constructed so as to be disposable whereby the empty bottle, nozzle and vial may be simply thrown away after use.

Apparatus of the type described above have, however, not proven to be entirely satisfactory for several reasons. In this connection one important aspect is in the dispensing of the douche concentrate into the diluent bottle. It is not uncommon during such dispensing as described above for the douche concentrate to spill from the vial as the latter is inverted. Additionally, the tip of the vial does not extend to any appreciable extent into the opening in the bottle so that the douche concentrate often leaks from between the vial and bottle during its dispensing. Furthermore, the open tip of the vial is relatively flimsy so that if the opening in the bottle is not perfectly formed, the vial tip may inadvertently contact an obstruction and, due to its lack of stiffness, tend to buckle. For all of these reasons, use of the prior art apparatus described above not infrequently results in spillage of the douche concentrate.

Additional problems in the prior art apparatus results from the particular material which forms the concentrate containing vial as well as the manner in which the same is constructed. Thus, such vials are generally formed of polypropylene or the like. However, polypropylene has a relatively high moisture vapor transmission rate when used with common douche concentrates. Further, the prior art vials are generally formed by molding which is a relatively expensive procedure.

SUMMARY OF THE INVENTION

Accordingly, one object of the present invention is to provide new and improved apparatus for storing and dispensing the components of a medicated douche solution for the subsequent application thereof.

Another object of the present invention is to provide new and improved apparatus for storing and dispensing components of a medicated douche wherein dispensing a medicated douche concentrate into a diluent can be accomplished without spillage and in a reliable manner.

Still another object of the present invention is to provide new and improved apparatus for storing and dispensing components of a medicated douche solution which is inexpensive in manufacture and which is formed of a material particularly suited for such use.

In accordance with the present invention, these and other objects are obtained by providing a sealed unitary packette comprising one component of the storing and dispensing apparatus and which is formed of a thin flexible plastic material, preferably Saran, and which contains a predetermined amount of liquid douche concentrate. The packette includes a container portion in which the douche concentrate is contained and a dispenser portion integral with the container portion which is constituted by an elongated substantially tubular stem having a very small inner diameter and a substantially constant transverse cross-section throughout its length. The apparatus also includes a sealed bottle containing a diluent and having a slanted connecting portion and wherein an opening is formable in the bottle.

Importantly, the major dimension of the constant transverse cross-section of the tubular stem of the packette is equal to a minimum value of the diameter of the opening formable in the diluent bottle. In other words, the diameter of the opening formable in the diluent bottle must be greater than the major dimension of the transverse cross-section of the tubular stem constituting the dispenser portion of the packette. Further, the diameter of the bottle opening must be less than a certain maximum value.

In order to dispense the douche concentrate into the diluent within the bottle, a terminal tip portion of the dispenser portion is separated therefrom whereupon the dispenser portion or tubular stem is inserted through the bottle opening. By virtue of its configuration, the dispenser portion can extend to a significant extent into the interior of the bottle so that the concentrate can be dispensed without any spillage by squeezing the container portion of the packette.

Finally, an elongate nozzle is provided which is connectable to the connecting portion of the bottle after the concentrate has been dispensed into the diluent.

According to a preferred embodiment, the maximum value of the diameter of the bottle opening is about 3/16 inch while the minimum opening diameter is about ⅛ inch. The elongated tubular stem constituting the dispenser portion has a length of at least about 0.5 inches.

According to another feature of the present invention, the elongated tubular stem of the packette has an inner diameter which is smaller than a certain value such that upon separating the terminal tip portion therefrom and orienting the packette with the free end of the tubular segment facing downwardly and without any squeezing pressure being applied to the container portion of the packette, the surface tension forces acting on the concentrate at the free end of the tubular stem will prevent the concentrate from freely flowing out of the packette. This is advantageous in that it is possible to prevent spillage of the concentrate from the packette even when the latter is inverted prior to inserting the dispenser portion thereof into the bottle opening.

According to another feature of the present invention, the packette is formed of a vinylidene chloride copolymer, such as known as Saran, using extruded tubular sheet material subsequently sealed in the appropriate configuration. Firstly, Saran material provides a reduced rate of moisture vapor transmission when used with conventional douche concentrates. Secondly, the particular method of manufacture is simpler and less expensive than that conventionally used for the same applications.

DESCRIPTION OF THE DRAWINGS

A more complete appreciation of the present invention and many of the attendant advantages thereof will be readily appreciated as the same becomes better understood by reference to the following detailed description when considered in connection with the accompanying drawings in which.

DESCRIPTION OF THE PREFERRED EMBODIMENTS

Figures 4, 5:
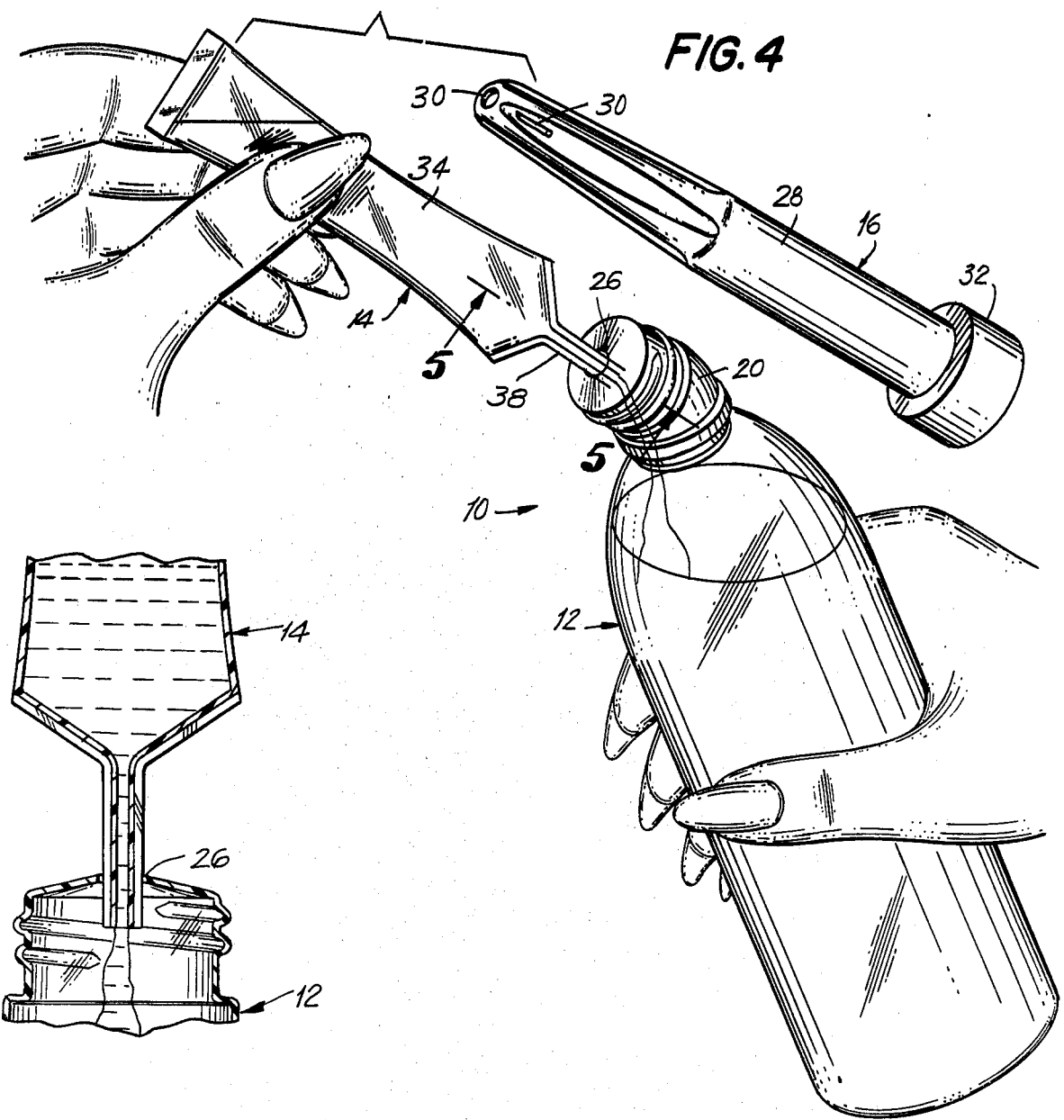
FIG. 4 is a perspective view of the diluent bottle and concentrate packette during the dispensing of the concentrate into the diluent and also illustrating a nozzle for use in connection with the invention.
FIG. 5 is a section view taken along line 5—5 of FIG. 4.

Referring now to the drawings wherein like reference characters designate identical or corresponding parts throughout the several views, and more particularly to FIG. 4 thereof, the apparatus for storing and dispensing components of a medicated douche solution according to the present invention, generally designated 10, comprises a sealed bottle 12 in which a predetermined amount of douche diluent, such as sanitized water, is contained, a packette 14 containing a predetermined amount of liquid douche concentrate, and a nozzle 16 adapted to be connected to the bottle after the concentrate has been dispensed into the diluent.

Figure 1:
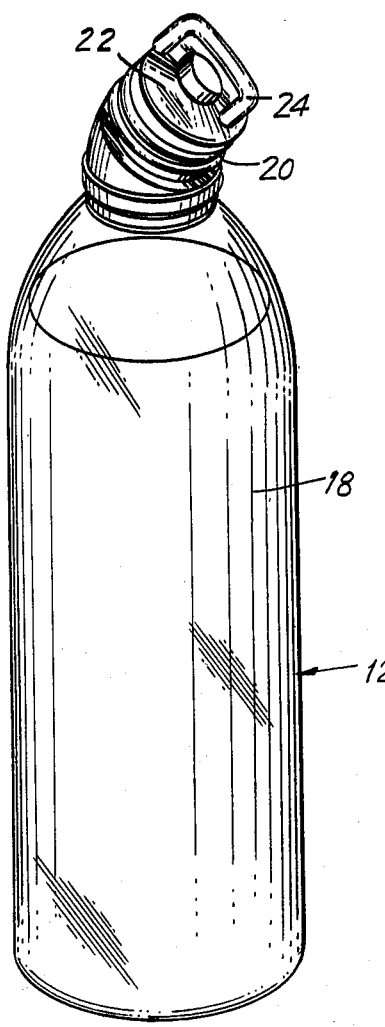
FIG. 1 is a perspective view of a sealed bottle containing a diluent for use in connection with the present invention.

Referring to FIG. 1, the bottle 12 which contains the douche diluent includes a main axially extending portion 18 and an integral substantially cylindrical threaded connecting portion 20 which is slanted with respect to the main portion 18, i.e., extends angularly with respect thereto. The connecting portion 20 is formed with a closure wall 22. A wing-shaped tab 24 is integrally formed on closure wall 22 which can be torn therefrom so as to form opening 26 therein for reasons to be described hereinbelow.

The bottle is formed of thin, flexible material and contains a predetermined amount of douche diluent such, for example, as 6 fluid ounces of sanitized water. The diluent will remain in a sanitized condition substantially indefinitely when the bottle is sealed, i.e., before the wing-shaped tab 24 is removed.

Subsequent to the dispensing of the douche concentrate into the diluent, described in greater detail hereinbelow, the nozzle 16 is connected to the bottle 12 for administering the douche solution contained within the bottle. Referring to FIG. 4, the nozzle 16 includes an elongated, hollow nozzle portion 28 having openings 30 formed at one of its ends and an internally threaded connecting portion 32 formed at its other end. Thus, after dispensing the concentrate into the diluent, the nozzle connecting portion 32 is screwed over the bottle connecting portion 20 in a conventional manner whereupon the nozzle is inserted into the vagina and a douche solution administered. By virtue of the slanted configuration of the connecting portion 20, insertion of the nozzle 16 is facilitated.

Figure 2:
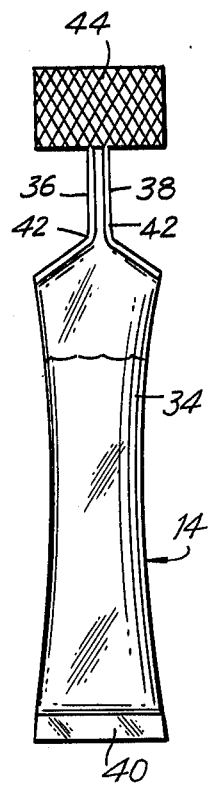
FIG. 2 is a side elevation view of a sealed packette containing douche concentrate according to the present invention.
Figure 3:
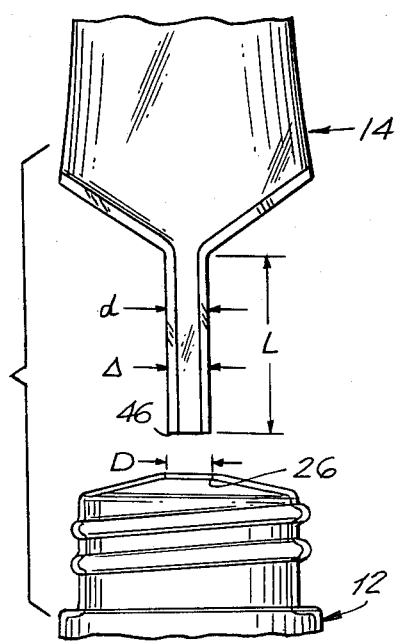
FIG. 3 is a detail view illustrating portions of the diluent bottle and packette in section just prior to insertion of the dispenser portion of the packette into the opening in the bottle.

Referring to FIG. 2, the packette 14 containing a predetermined amount of douche concentrate is illustrated. Thus, the packette 14 may contain 0.18 fluid ounces of suitable douche concentrate, such for example as Betadine douche concentrate available from The Purdue Frederick Company of Norwalk, Conn. Packette 14 is formed of thin, flexible plastic material, preferably Saran, and includes a container portion 34 defining an interior volume in which the douche concentrate is contained and a dispenser portion 36 integrally formed with the container portion 34. The dispenser portion 36 is constituted by an elongated, substantially tubuler stem 38 having a very small inner diameter $\Delta$ (FIG. 3). The tubular stem 38 has a substantially constant transverse cross-section throughout its length L (FIG. 3).

According to the invention, the major dimension d (FIG. 3) of the transverse cross-section of the elongated stem 38 constitutes a minimum value of the diameter D (FIG. 3) of the opening 26 formed in the bottle 12.

In the illustrated embodiment, the packette 14 is formed from an extruded tube of flexible plastic material, preferable Saran. A bottom edge band 40 is formed by ultrasonic sealing or the like as is a pair of side seal bands 42 which together define the tubular stem 38. A flat terminal tip portion 44 is formed at the outer end of the tubular stem 38 and consists of two plies of the Saran material welded to each other so as to close the tubular stem 38 to maintain the douche concentrate sealed within the packette. Thus, the dispenser portion 36 of packette 14 communicates at one end with the interior volume of container portion 34 and at its other end with terminal tip portion 44. The terminal tip portion 44 can be separated from the tubular stem 38 by tearing the same therefrom whereby the packette 14 is opened to allow the douche concentrate to be dispensed as described below.

The maximum value for the diameter or width d of the tubular stem 38 is preferably about 3/16 inch. Accordingly, the minimum possible diameter D of opening 26 is about 3/16 inch. The minimum length L of the elongated tubular stem 38 is preferably about 0.5 inches.

According to another feature of the present invention, the inner diameter $\Delta$ of the elongated tubular stem 38 is sufficiently small such that upon separating the terminal tip portion 44 from the stem 38 and orienting the packette 14 so that the free end of the tubular segment faces downwardly (as seen in FIG. 3), the surface tension forces acting on the concentrate at the free end of the tubular stem 38 will prevent the douche concentrate from freely flowing out of the packette. It has been found that utilizing conventional douche concentrates, such as Betadine mentioned above, a tubular stem 38 having an inner diameter $\Delta$ of about 1/16 inch will function in the manner described above.

A description of the use of the apparatus of the present invention will now be set forth. Firstly, the bottle 12 containing the douche diluent is opened by twisting off the wing-shaped tab 24 so as to form the opening 26 enclosure wall 22. The packette 14 is then opened by holding the same by the tubular stem 38 and tearing the terminal tip portion 44 therefrom. It is noted in this connection that the particular manner of constructing the packette, i.e., by suitably fusing double plied thicknesses of tubular extruded plastic material together, allows the terminal tip portion to be "torn" from the tubular stem 38 instead of actually being broken therefrom as in the case of the prior art molded vial described above.

Referring now to FIG. 3, the packette 14 is inverted and brought to the opening 26 of bottle 12. As noted above, by virtue of the fact that the inner diameter of the tubular stem 38 is below a certain maximum, the douche concentrate will be prevented from flowing under gravity out from the packette 14 by the surface tension forces acting at the free end 46 (FIG. 3) on the concentrate.

Referring now to FIGS. 4 and 5, the elongated substantially tubular stem 38 constituting the dispenser portion 36 of packette 14 is inserted through the bottle opening 26. By virtue of the fact that the length L of the tubular stem 38 is at least about 0.5 inches and preferably about ⅜ inches, the dispenser portion extends through the opening to a significant extent into the interior of the bottle. In this manner spillage of the concentrate during dispensing thereof into the diluent is reliably avoided.

Thus, as seen in FIG. 4, the concentrate is dispensed into the diluent by squeezing the container portion 34 of packet 14. The empty packette can be discarded.

The nozzle 16 is then connected to the bottle by screwing the nozzle connecting portion 32 over the bottle connecting portion 20. The bottle-nozzle combination is held upright and gently agitated to mix the diluent and concentrate in a thorough manner. The nozzle is then inserted into the vagina and the bottle squeezed to administer the douche solution until the latter is used up. After the douching operation, the empty bottle and nozzle can be discarded.

As seen from the foregoing, the present invention provides significant advantages relative to conventional apparatus presently in use. Thus, the douche concentrate can be dispensed into the diluent bottle in a reliable manner without the risk of spillage. The recognition of the use of Saran material for packette 14 is advantageous in that a significantly reduced rate of moisture vapor transmission is achieved. Furthermore, by forming the packette 14 of tubular flexible plastic material, construction costs are significantly reduced.

It is further seen that the provision of an elongated, substantially tubular stem as the dispensing portion of the packette 14 renders the same relatively stiff so that if the opening 26 is not fully formed after removal of the tab 24 and the end of the stem is obstructed for passing through the opening, the stem will not buckle or collapse which is also highly advantageous.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. Disposable apparatus for storing and dispensing the constituents of a medicated douche solution, comprising:
   a sealed bottle containing a predetermined amount of diluent, said bottle including a main axially extending portion and an integral substantially cylindrical connecting portion angularly extending from said main portion, said connecting portion being formed with a closure wall having means associated therewith for defining an opening therein having a diameter which is substantially equal to or less than a certain maximum value and which is substantially equal to or greater than a certain minimum value;
   a sealed unitary packette formed of a vinylidene chloride copolymer material containing a unit dose of liquid douche concentrate, said packette including a container portion defining an interior volume in which said unit dose of liquid douche concentrate is contained and a dispenser portion integral with said container portion and being constituted by an elongated substantially tubular stem having a substantially constant transverse cross-section throughout its length whose major dimension equals said minimum value of said bottle opening diameter, said tubular stem communicating at one end thereof with the interior of said container portion and having a separable integral terminal tip portion, said packette being openable through separation of said terminal tip portion from said dispenser portion, said tubular stem having a length greater than a certain value and an inner diameter smaller than a certain value such that upon opening said packette and inverting the same so that its open end faces downwardly, said tubular stem constitutes means for preventing the douche concentrate from freely flowing out of said packette under the effect of surface tension forces created between said stem and douche concentrate, said dispenser portion being insertable through said bottle opening so as to extend to a significant extent into the interior thereof so that the concentrate can be dispensed without spillage into the diluent by squeezing said container portion; and
   an elongate nozzle having a connecting portion adapted to be connected to said connecting portion of said bottle after said concentrate has been dispensed into the diluent.

2. The combination of claim 1 wherein said maximum value of said opening diameter is about 3/16 inch.

3. The combination of claim 2 wherein said minimum value is about ⅛ inch.

4. The combination of claim 2 wherein said elongated tubular stem constituting said dispenser portion has a length of at least about 0.5 inches.

5. The combination of claim 4 wherein said elongated tubular stem has an inner diameter of about 1/16 inch.

6. Apparatus for both storing and dispensing a liquid douche concentrate into a diluent bottle through an opening therein, comprising: a sealed unitary packette formed of a vinylidene chloride copolymer material, said packette including a container portion defining an interior volume in which a unit dose of liquid douche concentrate is contained and a dispenser portion integral with said container portion and being constituted by an elongated substantially tubular stem having a substantially constant transverse cross-section throughout its length, said dispenser portion communicating at one end thereof with the interior of said container portion and having a separable terminal tip portion, said vinylidene chloride copolymer material being air impermeable and both chemically and physically stable with respect to the liquid douche concentrate, said packette being normally sealed in an air-tight manner with the concentrate stored therein and openable through separation of said terminal tip portion, said tubular stem having a length greater than a certain value and an inner diameter smaller than a certain value such that upon opening said packette and inverting the same so that its open end faces downwardly, said tubular stem constitutes means for preventing the douche concentrate from freely flowing out of said packette under the effect of surface tension forces created between said stem and douche concentrate, whereupon said dispenser portion is insertable through the opening of a diluent bottle into the interior thereof so that the concentrate can be dispensed into the diluent by squeezing said container portion without spillage.

7. The combination of claim 6 wherein said elongated tubular stem constituting said dispenser portion has a length of at least about 0.5 inches.

8. The combination of claim 7 wherein said elongated tubular stem has an inner diameter of about 1/16 inches.

9. The combination of claim 6 wherein said container portion defines an interior adapted to store about 0.18 fluid ounces of said liquid douche concentrate.

10. The combination of claim 6 wherein said plastic material comprises transparent Saran material.

11. The combination of claim 10 wherein said Saran material has a thickness of about 0.006 inches.

12. The combination of claim 6 wherein said packette is formed of extruded tubular flexible plastic material having a bottom edge band and at least one side edge band.

* * * * *